(12) United States Patent
Tsao

(10) Patent No.: US 7,304,814 B2
(45) Date of Patent: Dec. 4, 2007

(54) COMPACT INFRARED SPECTROMETER, AND METHODS AND SYSTEMS FOR MANUFACTURE AND ASSEMBLY OF COMPONENTS USED IN SAME

(75) Inventor: Mei-Wei Tsao, Wilmington, DE (US)

(73) Assignee: Wilmington Infrared Technologies, Inc., Wilmington, DE (US)

( * ) Notice: Subject to any disclaimer, the term of this patent is extended or adjusted under 35 U.S.C. 154(b) by 55 days.

(21) Appl. No.: 11/444,051

(22) Filed: May 31, 2006

(65) Prior Publication Data

US 2006/0215166 A1 Sep. 28, 2006

Related U.S. Application Data

(62) Division of application No. 10/873,780, filed on Jun. 22, 2004, now Pat. No. 7,075,082.

(51) Int. Cl.
*G02B 7/02* (2006.01)
*G01J 5/02* (2006.01)
*G01J 3/40* (2006.01)
(52) U.S. Cl. .................. 359/819; 250/339.07; 356/305
(58) Field of Classification Search ................. 359/819
See application file for complete search history.

(56) References Cited

U.S. PATENT DOCUMENTS

| | | | |
|---|---|---|---|
| 3,877,812 A | 4/1975 | Thompson | |
| 4,690,507 A | 9/1987 | Zimmermann | |
| 4,773,756 A | 9/1988 | Blechinger | |
| 4,956,555 A | 9/1990 | Woodberry | |
| 5,005,934 A * | 4/1991 | Curtiss | 385/18 |

(Continued)

OTHER PUBLICATIONS

Elmore et al., Design and Performance of a Planar Array Infrared Spectrograph that Operates in the 3400 to 2000 cm Region, Applied Spectroscopy, 2002, 145-149, vol. 56, No. 2, Society for Applied Spectroscopy, USA.

(Continued)

*Primary Examiner*—Jordan Schwartz
*Assistant Examiner*—James C Jones
(74) *Attorney, Agent, or Firm*—Morgan, Lewis & Bockius LLP

(57) ABSTRACT

A compact spectrometer operable in a wavelength range of 4.5 or more microns includes an entrance slit, a collimating mirror, a grating, a focusing mirror and a first focal plane. At least some radiation passing through the slit follows an optical path in which at least some radiation passing through the slit is reflected by the collimating mirror onto the grating, which in turn reflects at least some radiation onto the focusing mirror, which in turn reflects and focuses at least some radiation at a first focal plane and onto the two-dimensional array of detectors. Each column in the two-dimensional array of detectors corresponds to a wavelength in the 4.5 or more micron range, the two-dimensional array includes a plurality of columns that collectively correspond to wavelengths spanning the 4.5 or more micron range, and each adjacent pair of columns in the two-dimensional array of detectors corresponds to two wavelengths that differ by an equal amount. The entrance slit, the collimating mirror, the grating, the focusing mirror and the first focal plane are positioned within a volume that is equal or less than 192 cubic inches in size.

10 Claims, 17 Drawing Sheets

U.S. PATENT DOCUMENTS

| | | | |
|---|---|---|---|
| 5,157,258 | A | 10/1992 | Gunning, III et al. |
| 5,166,755 | A | 11/1992 | Gat |
| 5,353,167 | A | 10/1994 | Kuklo et al. |
| 5,371,358 | A | 12/1994 | Chang et al. |
| 5,377,003 | A | 12/1994 | Lewis et al. |
| 5,420,681 | A | 5/1995 | Woodruff |
| 5,444,236 | A | 8/1995 | Ludington et al. |
| 5,483,335 | A | 1/1996 | Tobias |
| 5,519,219 | A | 5/1996 | Alexay et al. |
| 5,528,368 | A | 6/1996 | Lewis et al. |
| 5,539,518 | A | 7/1996 | Bennett |
| 5,714,758 | A | 2/1998 | Neu |
| 5,880,834 | A | 3/1999 | Chrisp |
| 5,883,712 | A | 3/1999 | Coffin |
| 6,031,233 | A | 2/2000 | Levin et al. |
| 6,069,695 | A * | 5/2000 | Rohr et al. ................. 356/318 |
| 6,236,508 | B1 | 5/2001 | Stapelbroek |
| 6,266,140 | B1 | 7/2001 | Xiang et al. |
| 6,303,934 | B1 | 10/2001 | Daly et al. |
| 6,322,040 | B1 | 11/2001 | Robertson et al. |
| 6,355,930 | B1 | 3/2002 | Sivathanu et al. |
| 6,420,708 | B2 | 7/2002 | Wilks, Jr. et al. |
| 6,693,280 | B2 | 2/2004 | Sting et al. |
| 6,784,428 | B2 | 8/2004 | Rabolt et al. |
| 6,862,092 | B1 | 3/2005 | Ibsen et al. |
| 6,980,295 | B2 | 12/2005 | Lemer |
| 2001/0048526 | A1 | 12/2001 | Bender |
| 2002/0109926 | A1* | 8/2002 | Horwitz ...................... 359/820 |
| 2002/0149777 | A1* | 10/2002 | Schreiber .................... 356/452 |
| 2003/0071216 | A1 | 4/2003 | Rabolt et al. |
| 2005/0051729 | A1 | 3/2005 | Chrisp |
| 2005/0264807 | A1 | 12/2005 | Lemer |

OTHER PUBLICATIONS

Manzardo et al., Miniaturization time-scanning Fourier transform spectrometer based on silicon technology, Optics Letters, Dec. 1, 1999, 1705-1707, vol. 24, No. 23, Optical Society of America, Switzerland.

Domanchin et al., Size and Spectrum, Photonics Spectra, July issue, Laurin Publishing.

Grandbois et al., Monitoring of phospholipid monolayer hydrolysis by phospholipase A2 by use of polarization-modulated Fourier transform infrared spectroscopy, Biophysical Chemistry 88, Jun. 16, 2000, 127-135, Elsevier.

Daly et al., Recent Advances In Miniaturization of Infrared Spectrometers, SPIE's Optoelectronics 2000, Jan. 22-28, 2000, 1-18.

Korb et al., Portable Fourier transform infrared spectroradiometer for field measurements of radiance and emissivity, Applied Optics, Apr. 1, 1996, 1679-1692, vol. 35, No. 10, Optical Society of America.

Yamamoto et al., Optical theory applied to infrared spectroscopy, Vibrational Spectroscopy, Jan. 10, 1994, 1-36, vol. 8, Elsevier Science B.V.

Diem et al., A Simple Algorithm to Convert Diode Array Spectral Data to Linear Wavelength or Wave Number Scales, Computer Enhanced Spectroscopy, 1986, 29-33, vol. 3.

Aryamanya-Mugisha et al., A Fourier Transform Diode Array Spectrometer for the UV, Visible, and Near-IR, Applied Spectroscopy, 1985, 693-697, vol. 39, No. 4, Society for Applied Spectroscopy.

Stout, Art, IR Cameras Break the Ice to Open Up New Markets, Photonics Spectra, Mar. 1996, 86-88.

Bleier et al., A Monolithic Interferometer for FT-IR Spectroscopy, Spec Sheet, PLX Inc., New York, USA.

Kruse et al., Elements of Infrared Technology: generation, transmission, and detection, 1962, Chapter 9, 321-385, John Wiley & Sons, Inc., New York, USA.

Skoog, Douglas A., Principles of Instrumental Analysis, 1985, Chapter 11, 315-355, Saunders College Publishing, USA.

Smith, et al., Modern Lens Design, A Resource Manual, 1992, Chapter 16, 271-301, McGraw-Hill, USA.

Buralli et al., A new generation of OSLO programs, Sinclair Optics Design Notes, vol. 5, No. 1—1994, pp. 1-12.

Boeing, SE-U20™/SE-U30™ Uncooled Imaging Electronics Product Overview, Version 2.0, Sensor Products Guidance, Navigation & Sensor, pp. 1-23.

Boeing, Gen II Production U3000A, Uncooled Microbolometer Infra Red Sensor, TV Image Format 320×240 Pixels, Sep. 1997, pp. 1-8.

Udson Technologies, Product Offerings, 1 pg.

Amber, A Raytheon Company, AE159-2 Si:Ga Focal Plane Array, Amber Report No. 94-12-04, 2 pgs.

Lockheed Martin, Santa Barbara Focalplane, SBF Staring Focalplane Array Family, ISO9001: 2000 and AS9100 Registered, 1 pg.

Electrophysics Corp., Tech Note, Infrared Viewing with PV-320 IR Imagers, pp. 1-7.

Ion Optics, Inc., [online] [retrieved on Apr. 25, 2000]. pulsIR Pulsed Infrared Radiator, Retrieved from Internet <URL http://www.ion-optics.com/pir_faq. htm>, 2 pgs.

Ion Optics, Inc., [online] [retrieved on Apr. 25, 2000]. Precision Infrared Calibration Source, Retrieved from Internet <URL http://www.ion-optics.com/calibration.htm>, 1 pg.

Boston Electronics Corporation, LC-IR-12 Series Miniature 9 Watt Infrared Emitter, pp. 1-7.

Ions Optics, Inc., [online] [retrieved on Apr. 25, 2000]. Micro-Spec, Handheld IR Spectrometer, Retrieved from Internet <URL http://www.ion-optics.com/spectdata.htm>, 2 pgs.

Wilks Enterprise, Inc., Applying Infrared Technology to the Real World, Variable Filter Array (VFA) Spectrometer, A New Concept in Infrared Instrumentation, 2 pgs.

Nexus, Nicolet Specification, Nexus™ FT-IR Spectrometer, Combining Superior FT-IR performance with exceptional versatility, pp. 1-4.

JACSO International Co., LTD., JASCO's Semiconductor Solutions, 2 pgs.

MIDAC Corporation, A Company in Motion, Specializing in FTIR innovation for over 20 years, FTIR Spectrometers, pp. 1-6.

Spectraline, Inc., 1 pg.

Ocean Optics, Inc., Still The Worlds' First Miniature Fiber Optic Spectrometer, Optical-sensing Systems For Thousands of UV, VIS and Shortwave NIR Applications, pp. 1-6.

Orbital Applied Instrument Technologies, Analect Hydrocarbon SmartSystem™, 2 pgs.

Orbital Applied Instrument Technologies, Analect Diamond20, FTIR Analyzer, 2 pgs.

Orbital, Applied Instrument Technologies, Analect® PCM™.

PittCon, Spectrascopy 15(5), May 2000, <URL http://www.spectroscopyonline.com>, 1 pg.

CODE V®, Optical Research Associates, Optical Design and Analysis Software, CODE V improves Your Iamge, pp. 1-8.

Hyperfine, Inc., Optical Technology For Advanced Applications, pp. 1-9.

Poenar, D.P. "Implementing an Integrated Infrared Spectrometer—a Theoretical Study" Proceedings of the SPIE, vol. 3740 (1999), p. 457-467.

Kansakoski, M. and Malinen, J. "Optical Characteristics of a PbS Detector Array Spectrograph for On-line Process Monitoring" Proceedings of the SPIE, vol. 3537 (1999), p. 80-87.

* cited by examiner

COMPACT INFRARED SPECTROMETER, AND METHODS AND SYSTEMS FOR MANUFACTURE AND ASSEMBLY OF COMPONENTS USED IN SAME

The present application is a divisional of U.S. patent application Ser. No. 10/873,780, filed Jun. 22, 2004 now U.S. Pat. No. 7,075,082, entitled "Compact Infrared Spectrometer, And Methods And Systems For Manufacture And Assembly Of Components Used In Same," the contents of which are incorporated herein in their entirety by reference.

FIELD OF THE INVENTION

The present relates to infrared spectrometers, and also to systems and methods for manufacturing and assembling optical components including components that may be used in infrared spectrometers.

BACKGROUND

Infrared spectroscopy had its origin when William Herschel discovered optical radiation beyond the red portion of the visible spectrum, which had been discovered by Isaac Newton. Since the $19^{th}$ century, the interaction between infrared radiation and different substances had been studied by scholars in the fields of both physics and chemistry. It has since been found that different materials absorb different portions of the infrared spectrum and these absorption features can be used to detect and identify chemical species. The first mass-produced infrared spectrometer was not built until World War II, when the US Office of Rubber Reserve identified the use of infrared spectroscopy as an effective means for measuring the compositions of the synthetic rubber compounds, and demanded the development of infrared spectrometers capable of operation from 1 μm and beyond. Since 1950, infrared spectrometers have gained wide acceptance by both the scientific and engineering communities. The first generation of these spectrometers utilized the optical dispersion of infrared radiation by rock salt materials such as sodium chloride (NaCl). Later these hygroscopic, or moisture-sensitive, rock salt prisms were replaced by diffractive gratings made with glass substrates. In general, these early infrared spectrometers weighed over 200 pounds, and were packaged in a space larger than 7 to 8 cubic feet in volume.

In addition to the dispersion-based infrared spectrometers, in late 1960s, with the advancements in lasers, computers and data storage devices, a new type of infrared spectrometer based on the principle of optical interferometry, was developed. Due to the computation involved in converting the interferometric measurements to optical spectra by the mathematical calculation of Fourier Transformation, these infrared instruments are also known in the infrared spectroscopy art as FTIR. Despite the fact that these FTIR spectrometers have provided highly improved sensitivity and spectral resolution compared to the dispersive infrared spectrometers, the interferometric nature of these instruments requires that ultimate environmental control be observed during their operation. This is because the interferometric measurements require the overlapping of two optical beams within the distance of half a wavelength, i.e., a precision in the micrometer range. In other words, any minute changes in the temperature or any small amount of vibration would result in failure to obtain useable spectra from such an FTIR spectrometer. Due to the incorporation of the optical interferometer and all the related feedback and control electronics, an FTIR usually weighs from 150 to 400 pounds and occupies a volume of 3 to 10 cubic feet.

For many modern industrial, security and military tasks, the abilities to detect the infrared spectral signatures of chemicals on the surface or in the atmosphere is highly valuable. These types of chemical information often can be used to determine the quality of a production process, or to evaluate the danger to approach or enter an area. However, due to the limitations in size, weight and ruggedness, infrared spectrometers have not been widely used as a first-line detection or monitoring tools for these applications, but rather as an off-line or laboratory validation tool.

To alleviate the practical limitations mentioned above, it would be desirable to develop a sensitive, light-weight, rugged and compact infrared spectrometer capable of detecting and/or identifying different chemical species under hostile service conditions. To achieve these goals, a compact optical spectrometer design is needed to cover a wide range of the infrared wavelengths, especially one that falls into the so-called "infrared fingerprint" (7-14 μm) region. This is because the infrared absorption features in the fingerprint region will provide the most distinctive chemical evidence that can be used to identify different substances.

While it could be straightforward to use the principles behind an FTIR to build smaller spectrometers that cover a wide range of the infrared spectrum, the low resistance to environmental changes may not meet the ruggedness requirements for field applications.

Another consideration related to the economics of the instrument is the ease of assembly. Inside all the infrared spectrometers today, the majority of the optical components found are made of glass materials. Whether it is the grating in a dispersive instrument or the mirrors within an FTIR, these glass-based components are often glued or clamped to mounts before they can be secured and then aligned. The accuracy of the gluing process, the possible shrinkage of the glue or epoxy and the chipping of the glass edges, all place uncertainties on the precision of the final alignment. As a result, these instruments need frequent maintenance or alignment after leaving the assembly line. Even during the assembly process, highly skilled opticians are required for proper alignment of all of these optical components, making the production more costly. The present invention provides a solution to these and other shortcomings found in the prior art.

SUMMARY OF THE INVENTION

In the present invention, a dispersive infrared spectrometer has been designed to work in tandem with two-dimensional infrared detectors. By tightly packing the optical paths within the spectrometer and carefully maintaining the divergence and convergence of the optical beams, the present invention achieves compactness while at the same time produces a focused infrared spectrograph on a two-dimensional detector which covers 4.5 or more microns of the infrared spectrum.

To further enhance the ruggedness of the spectrometer, all optical components and their mounting fixtures are fabricated from metals rather than glass, making the resulting spectrometer highly resistant to shocks and vibrations. Also, being dispersive rather than interferometric in its working principle, the spectrometer is significantly less vulnerable to the environmental changes.

In order to improve the ease of assembly and maintenance on such an infrared spectrometer, a push-and-lock mounting scheme is designed for optical components and component modules in this spectrometer. This simplifies the assembling process and at the same time achieves permanent alignment without the use of welding, brazing or gluing. In one embodiment, the assembly method does not require sophisticated optical testing for quality control purposes during the assembling process and is therefore more cost-effective. Finally, due to the rugged design and the permanent alignment, the spectrometer requires minimal maintenance once it is deployed, making it a more effective tool for field applications found in factories, public areas and battle fields. In one embodiment, the present invention is directed to a compact spectrometer operable in a wavelength range of 4.5 or more microns (preferably 7.5 to 13.5 microns or 4.5 or more microns within the 7.5 to 13.5 micron range). The spectrometer includes an entrance slit, a collimating mirror, a grating, a focusing mirror and a first focal plane. At least some radiation passing through the slit follows an optical path in which at least some radiation passing through the slit is reflected by the collimating mirror onto the grating, which in turn reflects at least some radiation onto the focusing mirror, which in turn reflects and focuses at least some radiation at a first focal plane and onto the two-dimensional array of detectors (which may be located at the first focal plane or another focal plane.) Each column in the two-dimensional array of detectors corresponds to a portion of the 4.5 or more micron range, the two-dimensional array includes a plurality of columns that collectively correspond to wavelengths spanning the 4.5 or more micron range, and each adjacent pair of columns in the two-dimensional array of detectors may correspond to wavelengths that differ by an equal amount. The entrance slit, the collimating mirror, the grating, the focusing mirror and the first focal plane are positioned within a volume that is equal or less than 192 cubic inches in size, and preferably satisfy some or all of the following design requirements:

1. Spacing among the components should be tightly arranged, yet cross-talk, undesired reflection or transmission and/or scattering should be reduced or eliminated;

2. The spatial and angular arrangement of the components should produce the desired wavelength coverage (on the detector array) without excessive aberration, such as spherical aberration, coma, astigmatism or chromatic aberration, and without excessive loss of the infrared energy passing through the slit;

3. In embodiments where the detector array (or infrared camera) is situated at a second focal plane (different from the first focal plane), the arrangement of the components preferably allows the infrared spectrum focused at the first focal plane (spectrograph) to be conveniently and efficiently relayed and refocused onto the two-dimensional array of detectors (or infrared camera) at the second focal plane;

4. The focused spectrum preferably utilizes the entire width of the two-dimensional detector array detector so that the spectral resolution is maximized; and 5. The height of the focused spectrum on the two-dimensional detector array is preferably maximized with minimal or no distortion so that a vertical average of pixels on the detector array (corresponding to the same wavelength) may be taken, or "binned", to enhance the signal-to-noise performance.

In accordance with a further aspect, the present invention is directed to a method for aligning and coupling an optical component to a substrate with a precision of at least 12.5 microns in position and 0.075 degrees in angular orientation. An optical component is machined from a material selected from aluminum, aluminum alloys, stainless steel, nickel, copper or beryllium. The optical component is affixed to a mount having a flat bottom surface that defines a first plane. A cylindrical rod extends away from the flat bottom surface of the mount at an angle perpendicular to the first plane, and at least first and second screws are disposed in first and second cylindrical openings that extend through the bottom surface of the mount. The first and second cylindrical openings in the mount are aligned perpendicular to the first plane and have an inner diameter that matches an outer diameter of the first and second screws. A substrate is provided having a flat upper surface that defines a second plane, wherein a first cylindrical opening extends from the upper surface of the substrate into the substrate at an angle perpendicular to the second plane, and wherein at least second and third threaded openings extend from the upper surface of the substrate into the substrate at an angle perpendicular to the second plane. The mount is positioned with respect to the substrate by simultaneously aligning the metal rod with the first opening in the substrate, the first opening in the mount with the second threaded opening in the substrate, and the second opening in the mount with the third threaded opening in the substrate. While the mount and the substrate are aligned, the cylindrical rod is inserted into the first cylindrical opening in the substrate until the bottom surface of the mount contacts the upper surface of the substrate. Following the inserting, friction between the cylindrical rod and the first opening in the substrate inhibits rotation of the mount about an axis perpendicular to the first and second planes, and tightness between the first opening in the substrate and the cylindrical rod restricts lateral movement of the mount with respect to the substrate. After the inserting, the first and second screws are rotated into the second and third threaded openings respectively in the substrate, whereby the mount is coupled to the substrate with said precision (i.e., at least 12.5 microns in position and 0.075 degrees in angular orientation.)

In accordance with a still further aspect, the present invention is directed to a method for aligning and coupling an optical component to a mount with a precision of at least 12.5 microns in position and 0.075 degrees in angular orientation. An optical component is machined from aluminum, aluminum alloys, stainless steel, nickel, copper or beryllium. The machining includes forming at least first, second and third cylindrical openings in the material, wherein the second and third cylindrical openings in the material are threaded. A cylindrical rod is positioned in the first cylindrical opening in the machined optical component, wherein the cylindrical rod extends away from a flat back surface of the optical component at an angle perpendicular to the flat back surface. A mount is provided having a flat front surface and at least first, second and third cylindrical openings that extend from the flat front surface into the mount at an angle perpendicular to the flat front surface. At least first and second of the plurality of cylindrical openings in the mount pass completely through a thickness of the mount, and first and second screws are respectively disposed in the first and second cylindrical openings in the mount. The first and second screws have an outer diameter that matches an inner diameter of the first and second cylindrical openings in the mount. Next, the mount is positioned with respect to the optical component by simultaneously aligning the metal rod extending from the optical component with the third opening in the mount, the second threaded opening in the optical component with the first opening in the mount, and third threaded opening in the optical component with the second opening in the mount. While the mount and the optical component are aligned, the cylindrical rod is pressed into the third cylindrical opening in the mount until the back surface of the optical component contacts the front surface of the mount. Following the inserting, friction between the cylindrical rod and the third opening in the mount inhibits rotation of the mount about an axis perpendicular to the front and back surfaces and tightness between the third cylindrical opening in the mount and the cylindrical rod restricts lateral movement of the mount with respect to the optical component. Thereafter, the first and second screws are rotated into the second and third threaded openings respectively in the optical component, whereby the mount is coupled to the optical component with said precision (i.e., at least 12.5 microns in position and 0.075 degrees in angular orientation.)

In accordance with a still further aspect, the present invention is directed to a method for forming a monolithic metal optical element. A mass of material (e.g., aluminum, aluminum alloys, stainless steel, nickel, copper or beryllium) is machined to form a monolithic component having a first face and a second face opposite the first face. The first face of the monolithic component comprises a focusing mirror or a collimating mirror. The machining is used to form a first cylindrical opening for receiving a cylindrical alignment rod that extends away from the second face at an angle perpendicular to a plane defined by the second face, a second cylindrical opening for receiving a first screw that extends away from the second face at an angle perpendicular to the plane defined by the second face, and a third cylindrical opening for receiving a second screw that extends away from the second face at an angle perpendicular to the plane defined by the second face. Alternatively, the second face of the optical element may be perpendicular to the first face, or any angle between parallel and perpendicular.

In accordance with yet a further aspect, the present invention is directed to a method for forming an optical grating element. A mass of material (e.g., aluminum, aluminum alloys, stainless steel, nickel, copper or beryllium) is machined to form a first face of the optical grating element, a first cylindrical opening that extends from the first face into the material at an angle perpendicular to the first face, a second cylindrical opening for receiving a first screw that extends from the first face into the material at an angle perpendicular to the first face, and a third cylindrical opening for receiving a second screw that extends from the first face into the material at an angle perpendicular to the first face. A cylindrical alignment rod is inserted into the first cylindrical opening, wherein, after the inserting, the cylindrical alignment rod extends away from the material at an angle perpendicular to the first face. A second face of the optical grating element is fabricated using an epoxy replication process, wherein the second face is perpendicular to the first face, the second face is formed from a resin layer bonded to the machined material, and the second face comprises an optical grating. Alternatively, the second face of the optical grating element may be parallel to the first face, or any angle between parallel and perpendicular.

DETAILED DESCRIPTION OF THE PREFERRED EMBODIMENT

Figure 1:
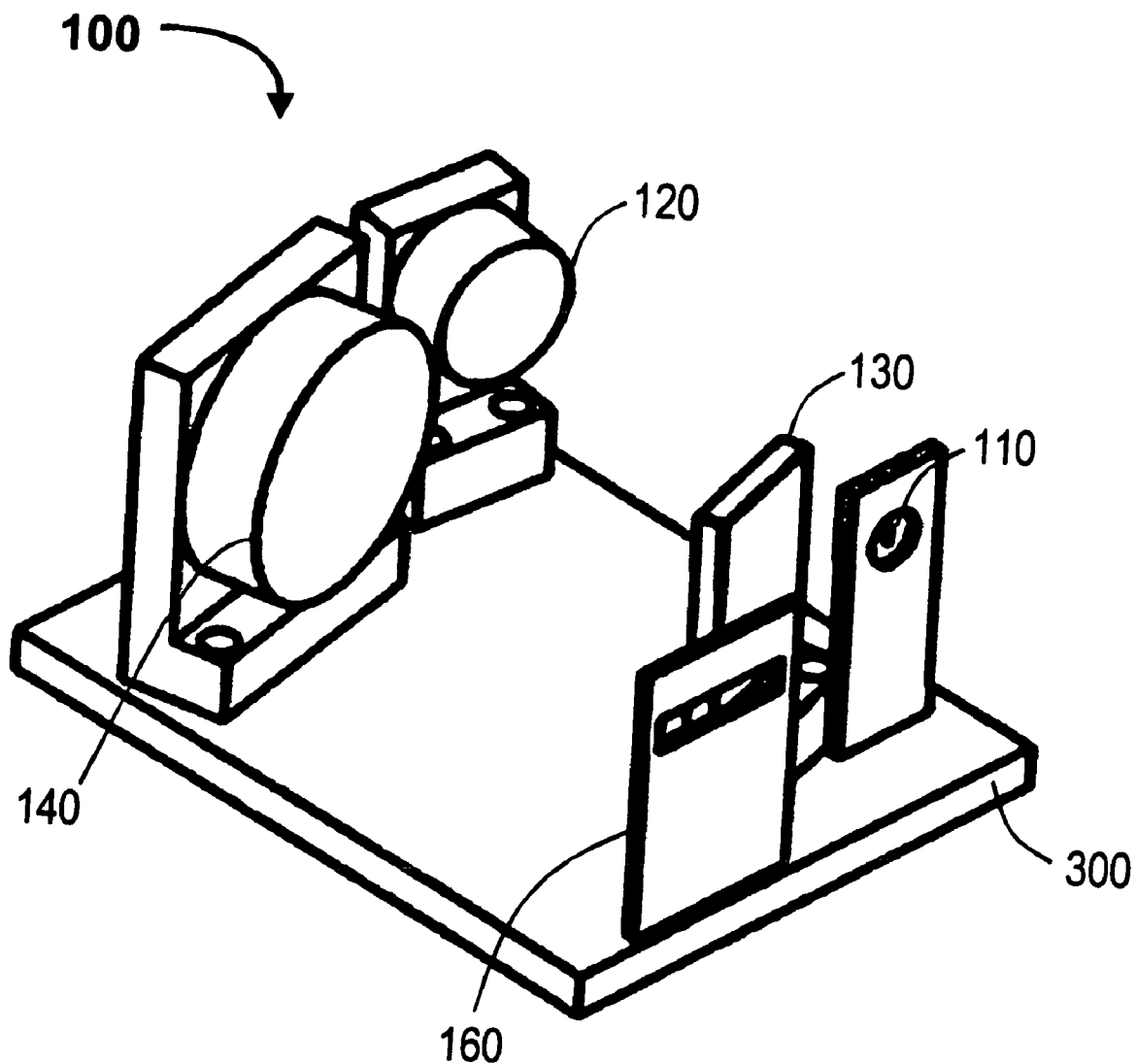
FIG. 1 is an isometric view of an infrared spectrometer in accordance with the present invention.
Figure 2:
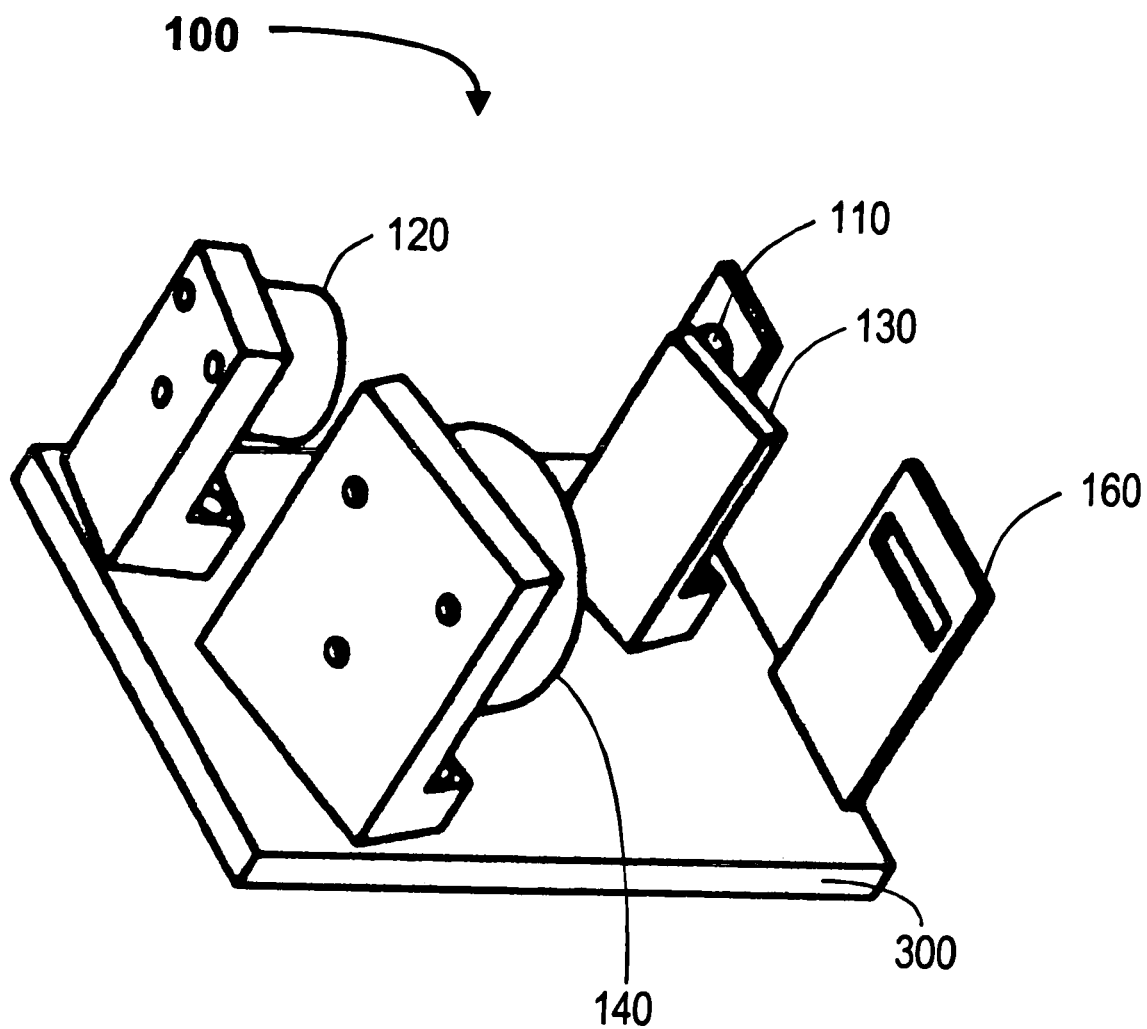
FIG. 2 is a further view of the infrared spectrometer shown in FIG. 1.

FIGS. 1 and 2 illustrate different views of an infrared spectrometer 100 in accordance with the present invention. Spectrometer 100 is compact (e.g., less than 192 cubic inches in volume as described below), and operable in a wavelength range of 4.5 or more microns. In one embodiment, spectrometer 100 operates in the 7.5 to 13.5 micron range and, in a yet more specific embodiment, spectrometer 100 operates in 4.5 or more microns of the 7.5 to 13.5 micron range. In other embodiments, spectrometer 100 operates in 4.5 or more microns of the 3.0 to 14.5 micron range.

Figure 3:
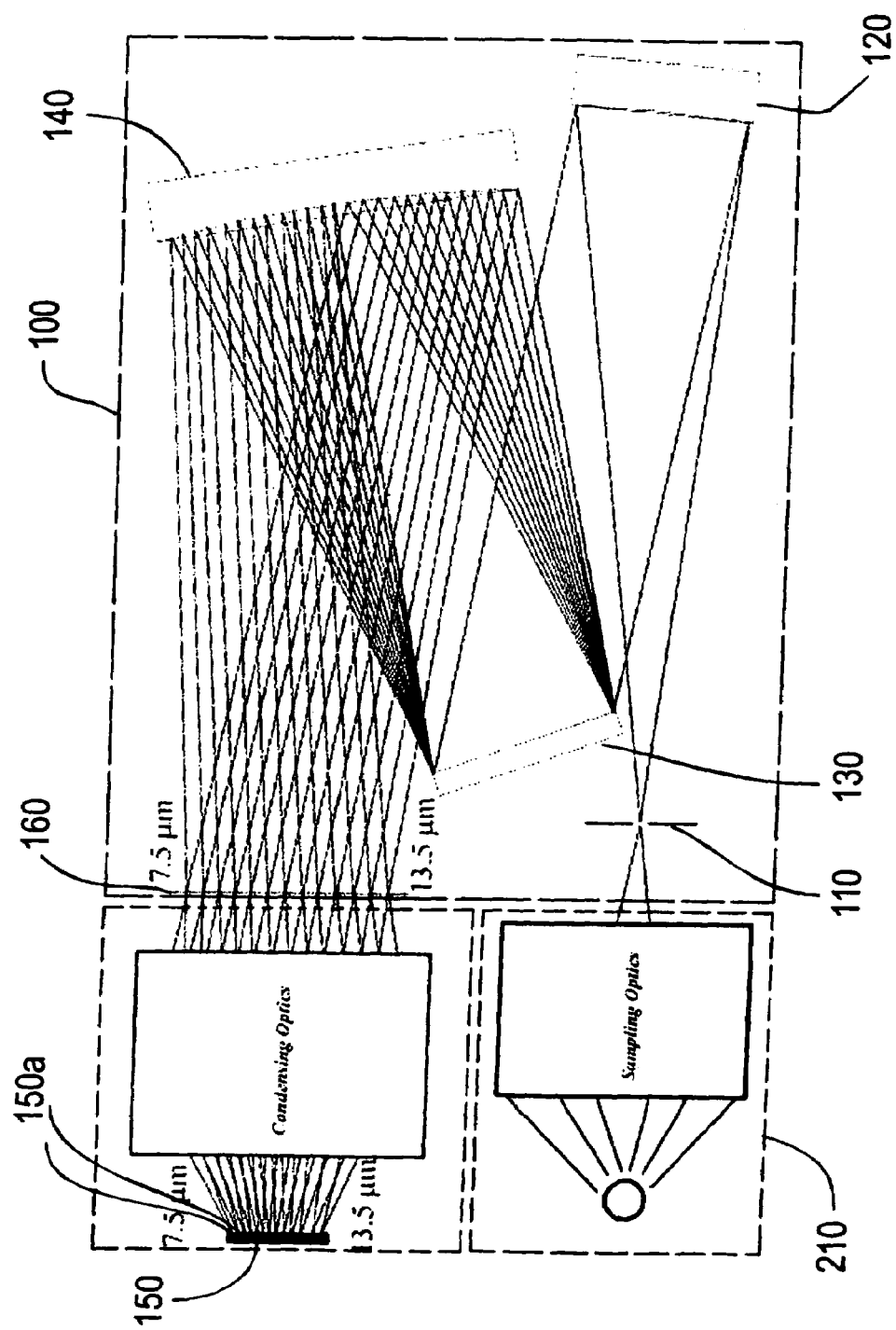
FIG. 3 is a diagram showing the optical path of infrared radiation in the spectrometer shown in FIGS. 1-2, and sampling and condensing optics.
Figure 4A:
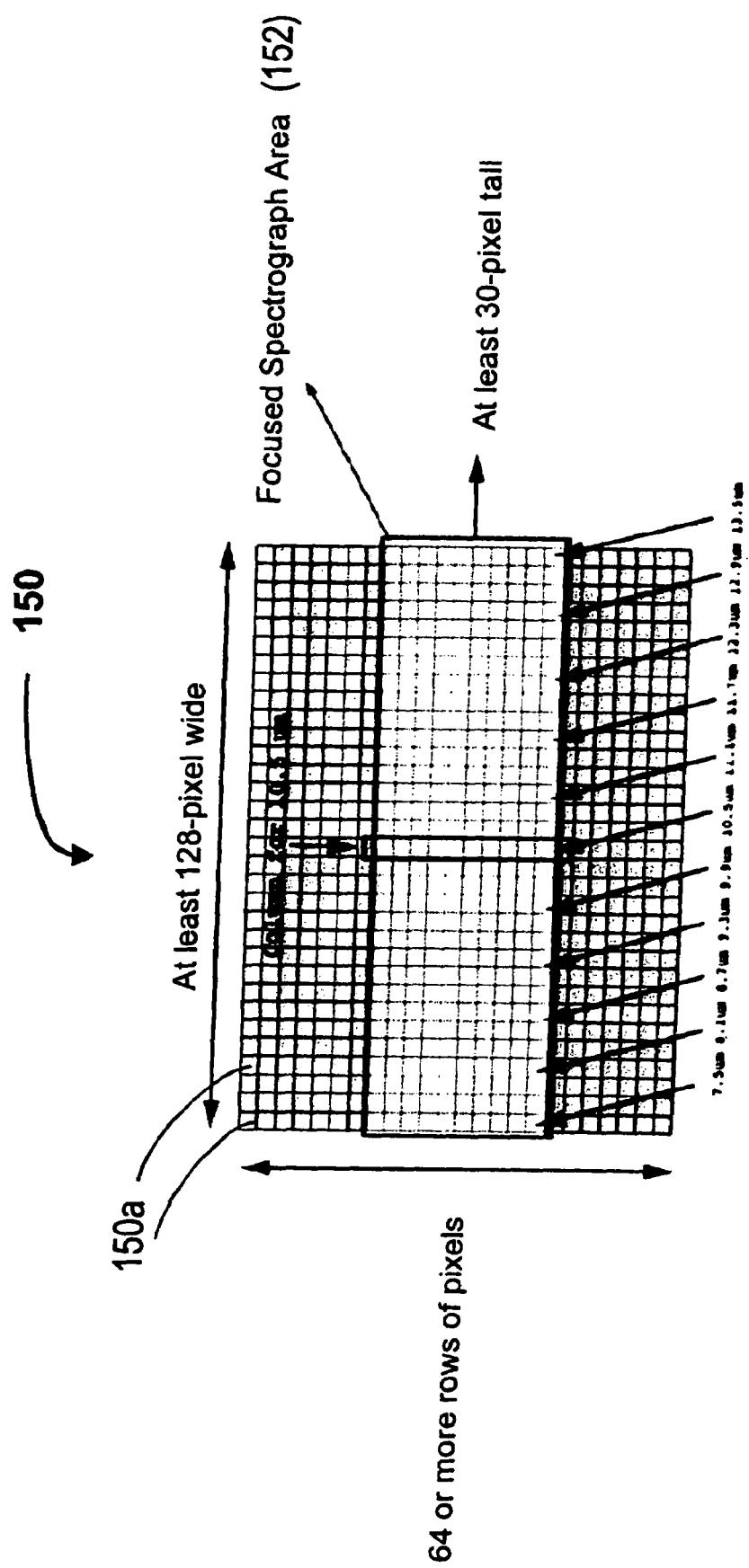
FIG. 4A illustrates the relationship between the rows and columns of pixels in the planar detector and a wavelength coverage of 6 microns, in accordance with the present invention.
Figure 4B:
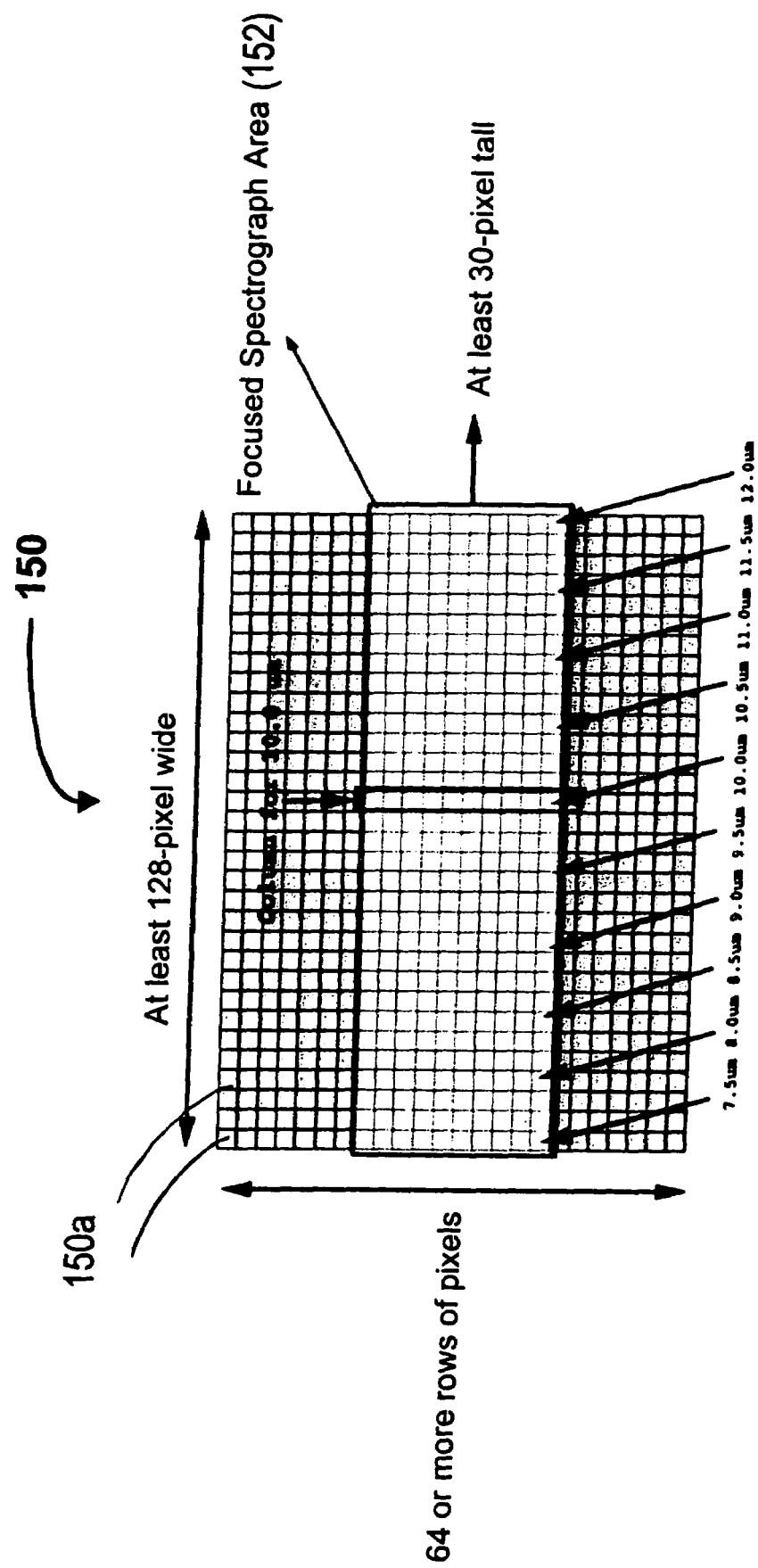
FIG. 4B illustrates the relationship between the rows and columns of pixels in the planar detector and a wavelength coverage of 4.5 microns, in accordance with the present invention.

Spectrometer 100 includes an entrance slit 110, a collimating mirror 120, a grating 130 and a focusing mirror 140. As shown in FIG. 3, at least some radiation passing through slit 110 follows an optical path in which at least some radiation passing through slit 110 is reflected by the collimating mirror 120 onto the grating 130, which in turn reflects at least some radiation onto the focusing mirror 140, which in turn reflects and focuses at least some radiation at a first focal plane 160 and onto the two-dimensional array of detectors 150 (which may be located at the first focal plane or another focal plane.) As shown in FIGS. 4A, 4B, the two-dimensional detector array 150 preferably has 128 or more pixels per row; in a particularly preferred embodiment a detector array that is 160 pixels wide by 120 pixels high may be used. The height of the focused spectrum 152 on the two-dimensional detector array is preferably maximized with minimal or no distortion so that a vertical average of pixels on the detector array (corresponding to the same wavelength) may be taken, or "binned", to enhance the signal-to-noise performance. In preferred embodiments, vertical binning of 30 or more pixels is used to enhance signal-to-noise performance; in a particularly preferred embodiment, vertical binning of 50 or more pixels may be used. A high read-out speed is preferably applied to the detector array to further enhance the signal-to-noise ratio (e.g., 30 full sets of array data per second, or more, is desired and 60 full sets of array data is even more preferable). Due to ambient temperature fluctuations, it may be necessary to frequently calibrate the detector array in order to achieve data stability over continuous operation. Manual or automatic fluctuation compensation triggered by periodic and/or event-based logic may used to calibrate the detector array.

As shown in FIGS. 3 and 4, each column 150a in the two-dimensional array of detectors corresponds to a portion of the 4.5 or more micron range. The two-dimensional array includes a plurality of columns 150a that collectively correspond to wavelengths spanning the 4.5 or more micron range, and each adjacent pair of columns 150a in the two-dimensional array of detectors may correspond to wavelengths that differ by an equal amount. In one embodiment, the entrance slit 110, the collimating mirror 120, the grating 130, the focusing mirror 140 and the first focal plane 160 are positioned within a volume that is equal or less than 192 cubic inches in size.

Figure 5A:
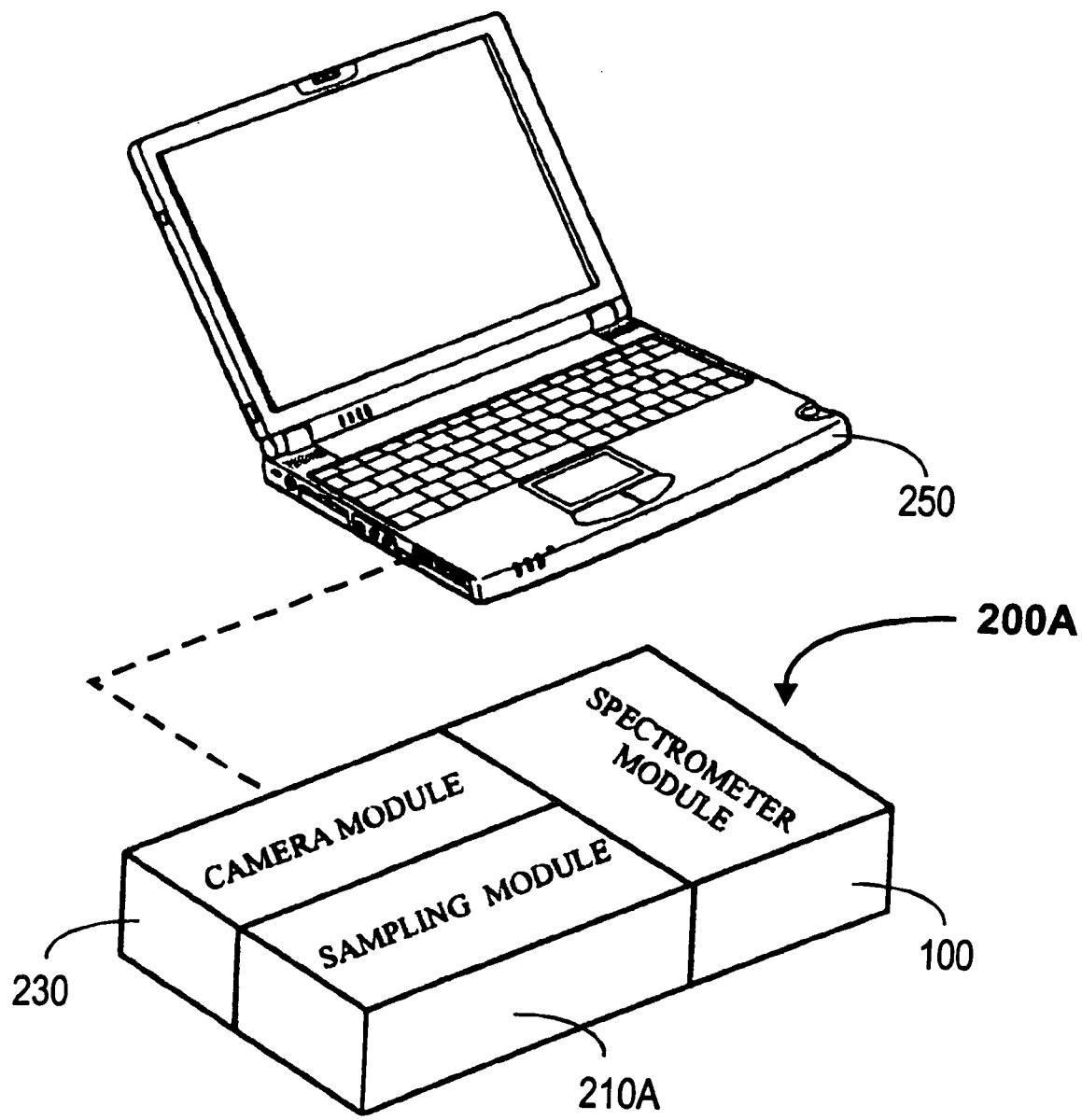
FIG. 5A illustrates an integrated, compact packaging for housing a spectrometer, optics, a detector and electronics, in accordance one embodiment of the present invention.

Referring now to FIG. 5A, there is shown an integrated, compact packaging 200A for housing spectrometer 100, as well as other components. Sampling module 210A functions to direct IR energy to the entrance slit 110 of spectrometer 100. Camera module 230 houses the detector (shown, e.g., in FIG. 4A, 4B). In one embodiment, the total volume of compact packaging 200A is less than about 700 cubic inches. A computer-based control module 250 is optionally used for operating components in packaging 200A, and for receiving data therefrom.

Figure 5B:
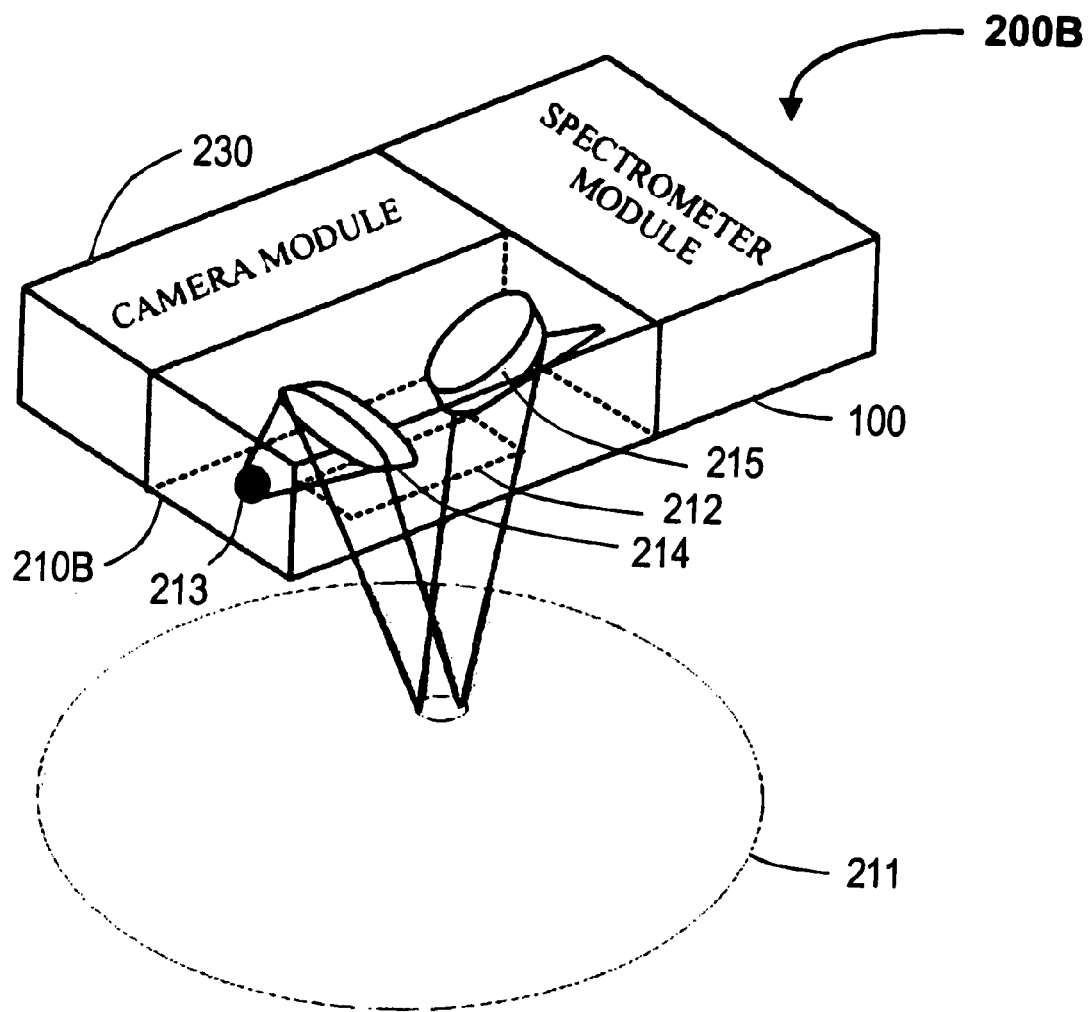
FIG. 5B illustrates an integrated, compact packaging for housing a spectrometer, optics, a detector and electronics, in accordance a further embodiment of the present invention.

Referring now to FIG. 5B, a further embodiment of an integrated, compact packaging 200B for housing spectrometer 100, as well as other components is shown. This embodiment may be used for surface detection, e.g., for sampling a surface 211 such as a silicon wafer, a coating or a drug tablet surface. In this embodiment, the sampling module 210B projects IR energy from IR source 213 through slot opening 212 to the surface 211 of the sample via collecting mirror 214, then the reflected IR energy is redirected and refocused into the slit 110 of spectrometer module 100 using focusing mirror 215. In one embodiment, the total volume of compact packaging 200B is less than about 700 cubic inches, and a computer-based control module 250 (as shown in FIG. 5A) is optionally used for operating components in packaging 200B, and for receiving data therefrom.

Figure 5C:
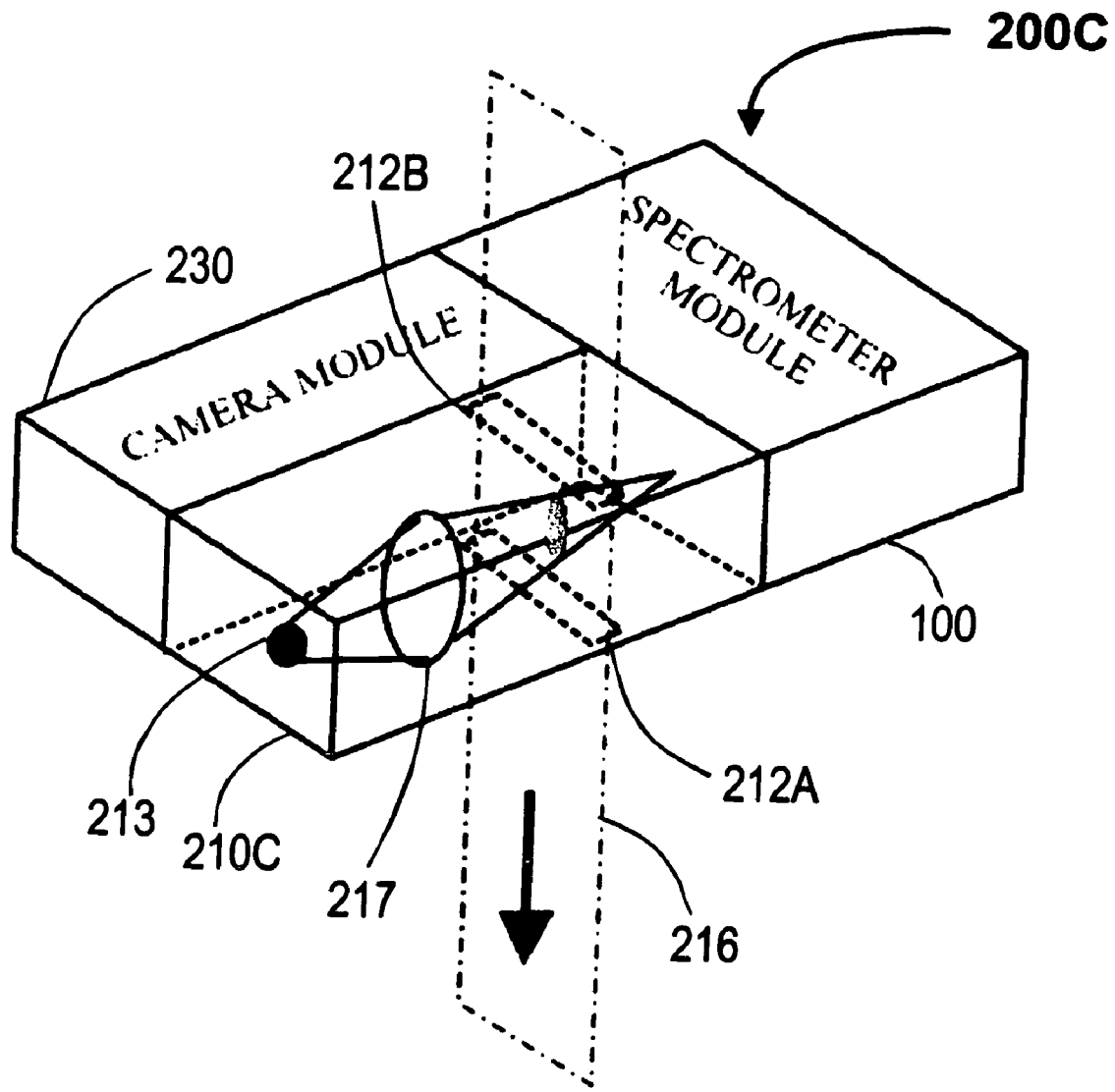
FIG. 5C illustrates an integrated, compact packaging for housing a spectrometer, optics, a detector and electronics, in accordance a still further embodiment of the present invention.

Referring now to FIG. 5C, a still further embodiment of an integrated, compact packaging 200C for housing spectrometer 100, as well as other components is shown. This embodiment may be used for measuring a continuously moving sample 216. In this embodiment, the sampling module 210C directs and focuses IR energy (originating from IR source 213 and focused using focusing lens 217) to slit 110 of the spectrometer module 100 while the moving sample 216 passes through the optical path in order to continuously measure sample 216. Slot openings 212A and 212B are provided to allow moving sample 216 to pass through sampling module 210C. Static samples can also be measured by placing them in the optical path using the embodiment shown. In one embodiment, the total volume of compact packaging 200C is less than about 700 cubic inches, and a computer-based control module 250 (as shown in FIG. 5A) is optionally used for operating components in packaging 200C, and for receiving data therefrom.

Figure 5D:
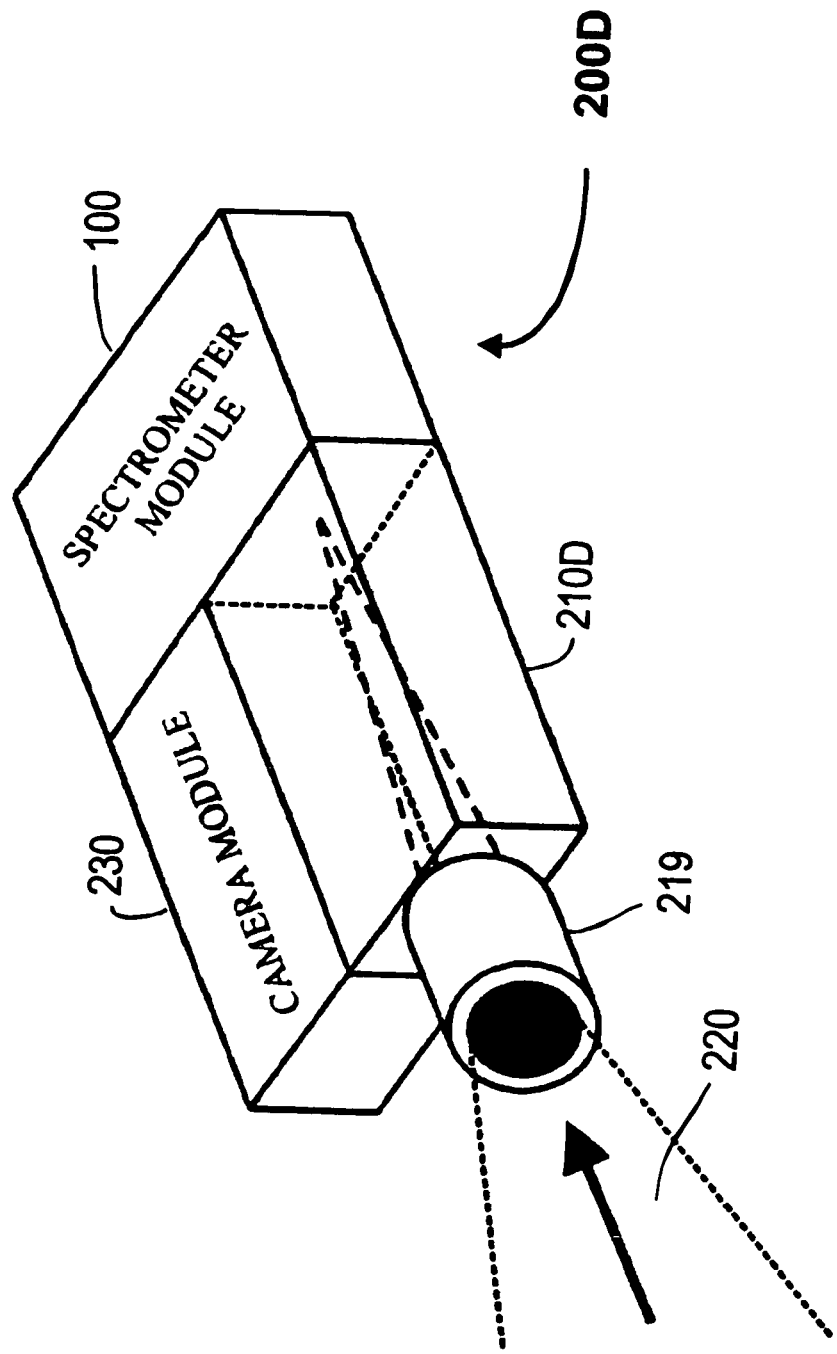
FIG. 5D illustrates an integrated, compact packaging for housing a spectrometer, optics, a detector and electronics, in accordance yet a further embodiment of the present invention.

Referring now to FIG. 5D, a still further embodiment of an integrated, compact packaging 200D for housing spectrometer 100, as well as other components is shown. This embodiment may be used for collecting and sampling distant IR energy 220. In this embodiment, the sampling module 210D directs and focuses IR energy (using telescopic optics 219) onto slit 110 of the spectrometer module 100. In one embodiment, the total volume of compact packaging 200D is less than about 700 cubic inches, and a computer-based control module 250 (as shown in FIG. 5A) is optionally used for operating components in packaging 200D, and for receiving data therefrom.

Figure 6:
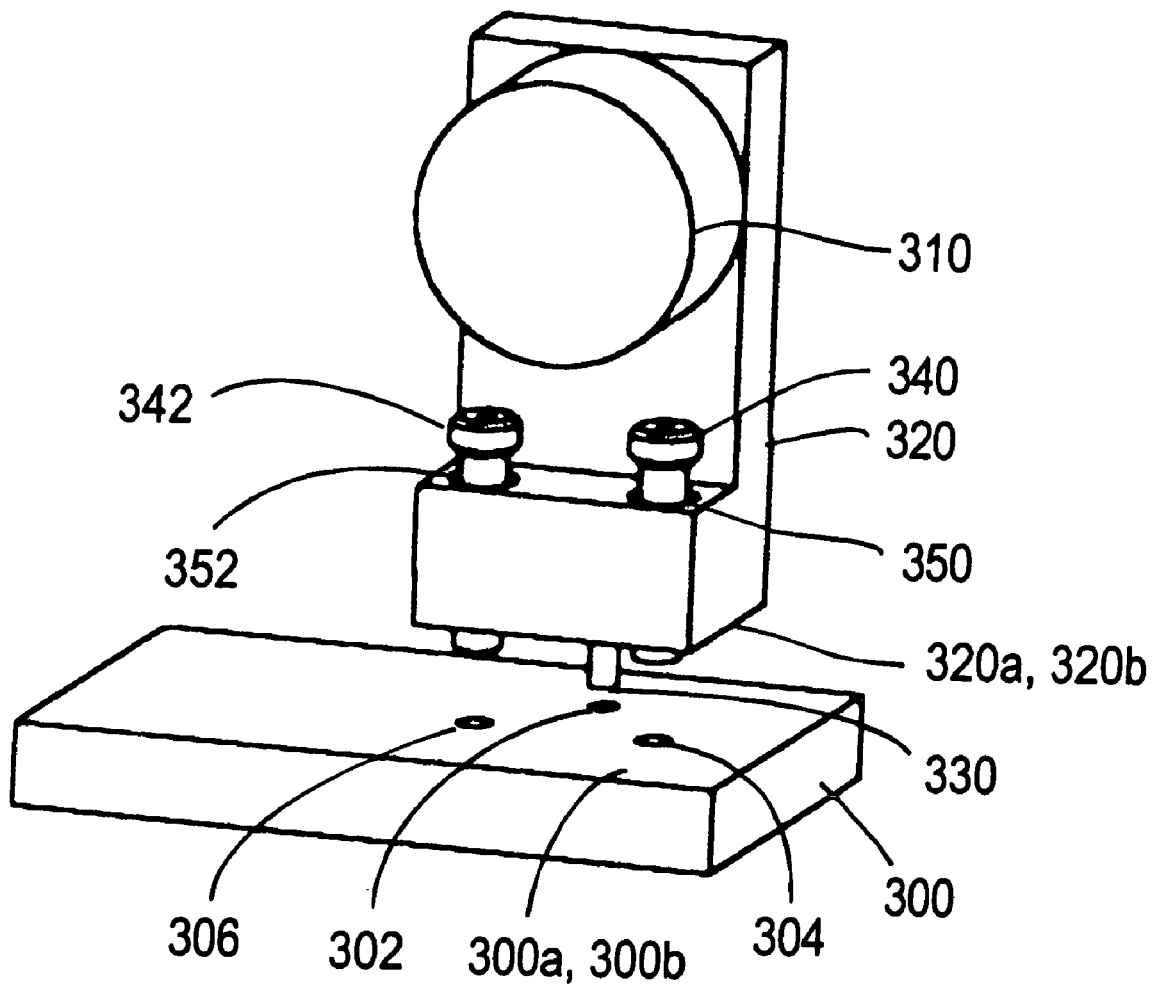
FIGS. 6-7 illustrate a system for aligning and coupling an optical component to a substrate, in accordance with the present invention.
Figure 7:
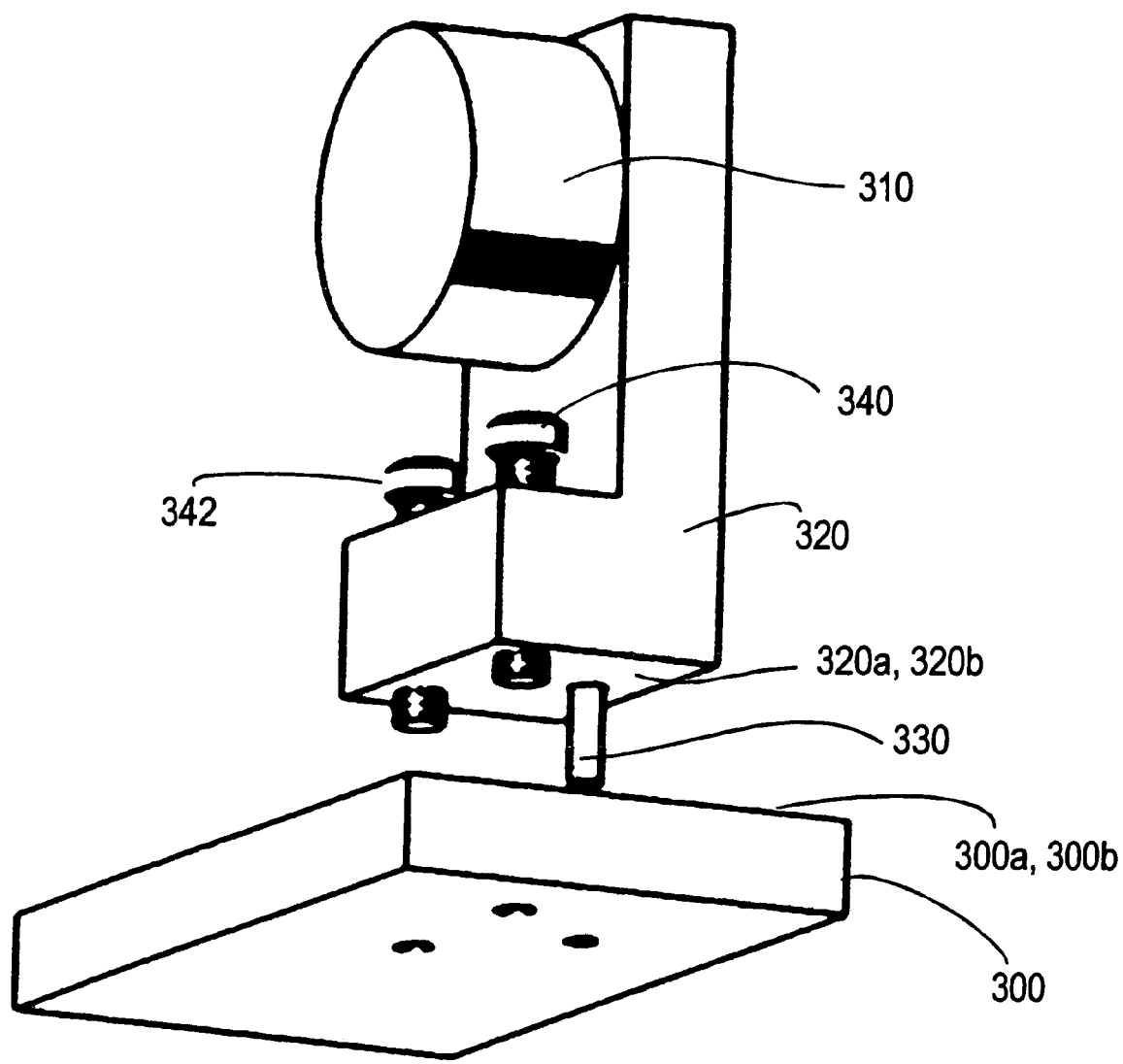
Figure 8:
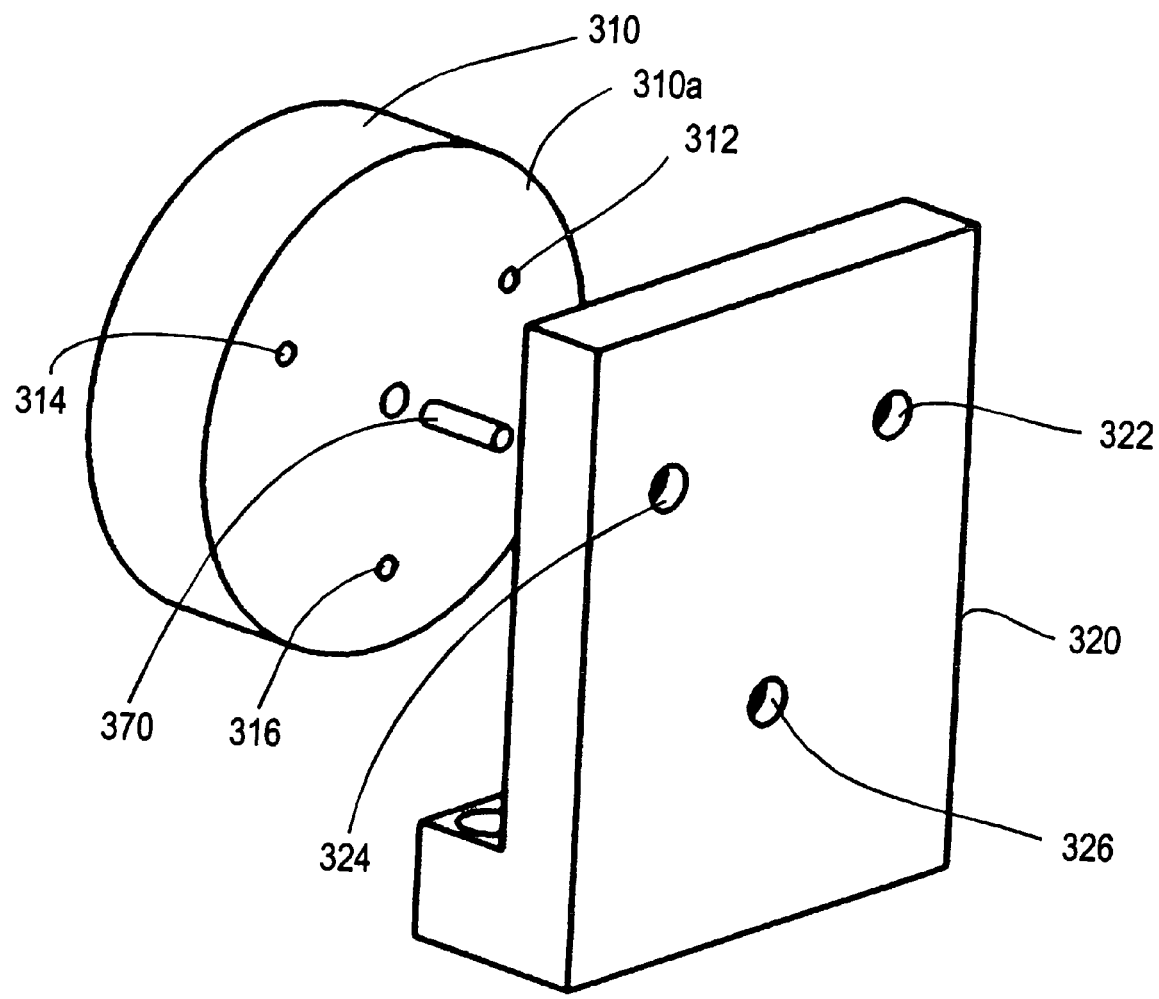
FIGS. 8-11 illustrate a system for aligning and coupling an optical component to a mount, in accordance with the present invention.
Figure 9:
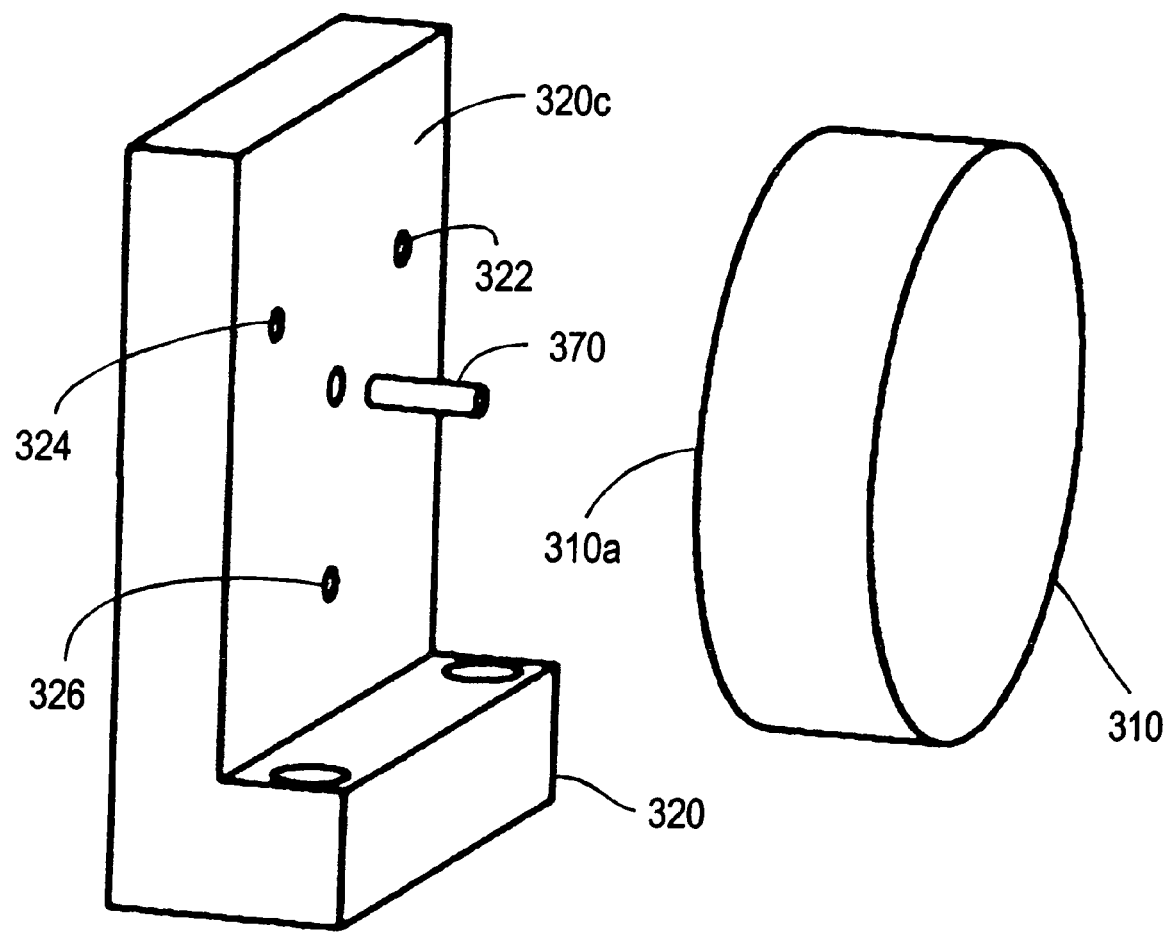
Figure 10:
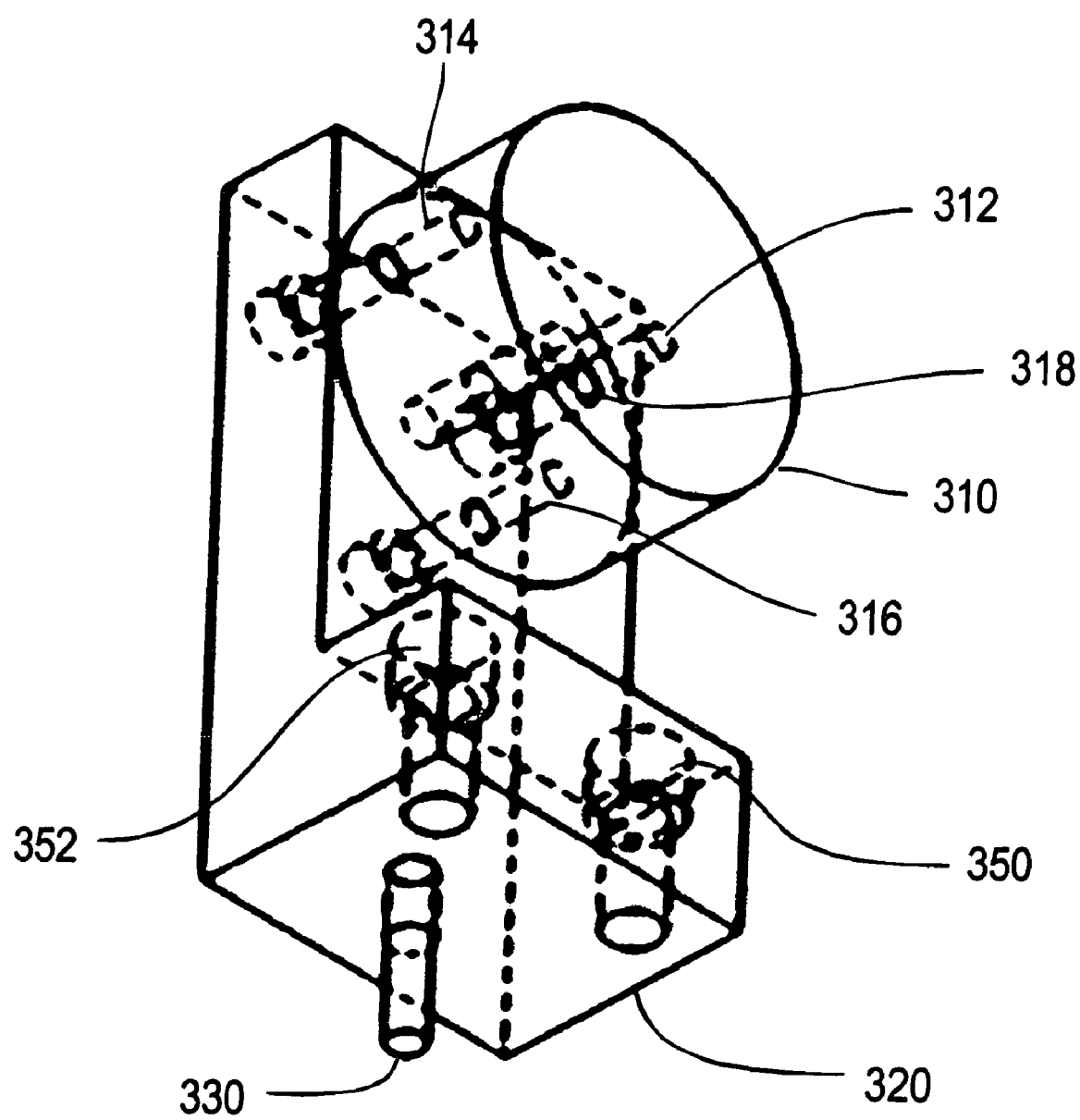
Figure 11:
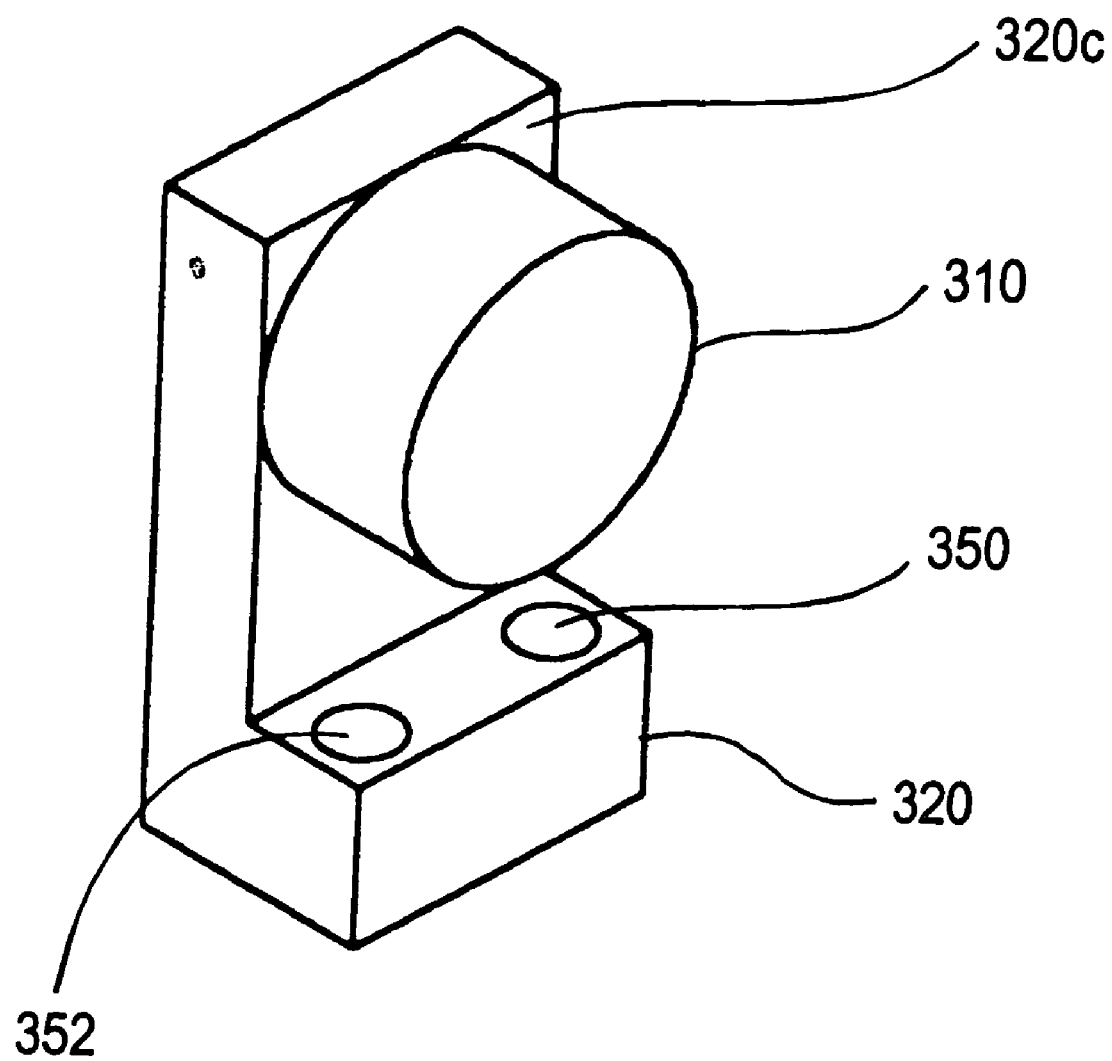

FIGS. 6 and 7 illustrate a system for aligning and coupling an optical component 310 (e.g., collimating mirror 120, grating 130 or focusing mirror 140 of spectrometer 100) to a substrate 300 (e.g., the base of spectrometer 100), in accordance with the present invention. In one embodiment, the system aligns and couples optical component 310 to substrate 300 with a precision of at least 12.5 microns in position and 0.075 degrees in angular orientation. Optical component 310 is initially machined from a material selected from aluminum, aluminum alloys, stainless steel, nickel, copper or beryllium. Optical component 310 is then affixed to a mount 320, which has a flat bottom surface 320a that defines a plane 320b. Mount may be formed from any of the following materials: aluminum, aluminum alloys, stainless steel, nickel, copper, beryllium, titanium, aluminum composite, graphite or graphite composites. Coupling of optical component 310 to mount 320 is explained in further detail in connection with FIGS. 8-11 below.

Referring again to FIGS. 6 and 7, a cylindrical rod 330 extends away from flat bottom surface 320a of the mount 320 at an angle perpendicular to plane 320b, and first and second screws 340, 342 (in other embodiments additional screws may be used) are disposed in first and second cylindrical openings 350, 352, that extend through the bottom surface 320a of the mount. The first and second cylindrical openings 350, 352 in the mount are aligned perpendicular to plane 320b and have an inner diameter that matches an outer diameter of screws 340, 342.

Substrate 300 has a flat upper surface 300a that defines a further plane 300b. Substrate 300 may be formed from any of the following materials: aluminum, aluminum alloys, stainless steel, nickel, copper, beryllium, titanium, aluminum composite, graphite or graphite composites. A cylindrical opening 302 extends from the upper surface 300a of the substrate into substrate 300 at an angle perpendicular to plane 300b. Threaded openings 304, 306 extend from the upper surface 300a of the substrate into the substrate at an angle perpendicular to plane 300b.

The mount 320 is positioned with respect to the substrate 300 by simultaneously aligning metal rod 330 with opening 302 in the substrate, opening 350 in the mount with threaded opening 304 in the substrate, and opening 352 in the mount with threaded opening 306 in the substrate. While the mount 320 and substrate 300 are aligned, rod 330 is inserted into the cylindrical opening 302 in the substrate until the bottom surface 320a of the mount contacts the upper surface 300a of the substrate. Following the inserting, friction between the rod 330 and opening 302 in the substrate inhibits rotation of mount 320 about an axis perpendicular to the planes 300a, 320a, and tightness between opening 302 in the substrate and rod 330 restricts lateral movement of mount 320 with respect to the substrate 300. After the inserting, screws 340, 342 are rotated into threaded openings 350, 352, respectively in the substrate, thereby coupling mount 320 to substrate 300 with a precision of at least 12.5 microns in position and 0.075 degrees in angular orientation.

FIGS. 8-11 illustrate a system for aligning and coupling an optical component 310 to a mount 320, in accordance with the present invention. In one embodiment, the system aligns and couples optical component 310 to mount 320 with a precision of at least 12.5 microns in position and 0.075 degrees in angular orientation. As mentioned above, optical component 310 is initially machined from aluminum, aluminum alloys, stainless steel, nickel, copper or beryllium. The machining includes forming cylindrical openings 312, 314, 316, 318 in the material, wherein cylindrical openings 312, 314, 316 are threaded. (It will be understood that fewer or additional openings could be used in conjunction with matching screws). Cylindrical rod 370 is positioned in cylindrical opening 318 in the machined optical component, such that rod 370 extends away from a flat back surface 310a of the optical component at an angle perpendicular to the flat back surface 310a.

Mount 320 has a flat front surface 320c and openings 322, 324, 326 that extend from the flat front surface 320c into the mount at an angle perpendicular to flat front surface 320a. At least two of the openings 322, 324, 326 in the mount preferably pass completely through a thickness of the mount, and first and second screws (not shown) are respectively disposed in two of the cylindrical openings 322, 324, 326 in the mount. The first and second screws have an outer diameter that matches an inner diameter of openings 322, 324, 326 in the mount.

Next, the mount 320 is positioned with respect to the optical component 310 by simultaneously aligning the metal rod 370 extending from the optical component with opening 318 in the mount, threaded opening 312 in the optical component with the opening 322 in the mount, and threaded opening 314 in the optical component with opening 324 in the mount. While mount 320 and the optical component 310 are aligned, cylindrical rod 370 is pressed into the cylindrical opening 318 in the mount until the back surface 310a of the optical component contacts the front surface 320c of the mount. Following the inserting, friction between cylindrical rod 370 and opening 318 in the mount inhibits rotation of the mount 320 about an axis perpendicular to surfaces 310a, 320c, and tightness between cylindrical opening 318 in the mount and cylindrical rod 370 restricts lateral movement of the mount 320 with respect to the optical component 310. Thereafter, two screws (not shown) are rotated into the threaded openings 312, 314 respectively in the optical component, thereby coupling mount 320 to optical component 310 with a precision of at least 12.5 microns in position and 0.075 degrees in angular orientation.

Figure 12:
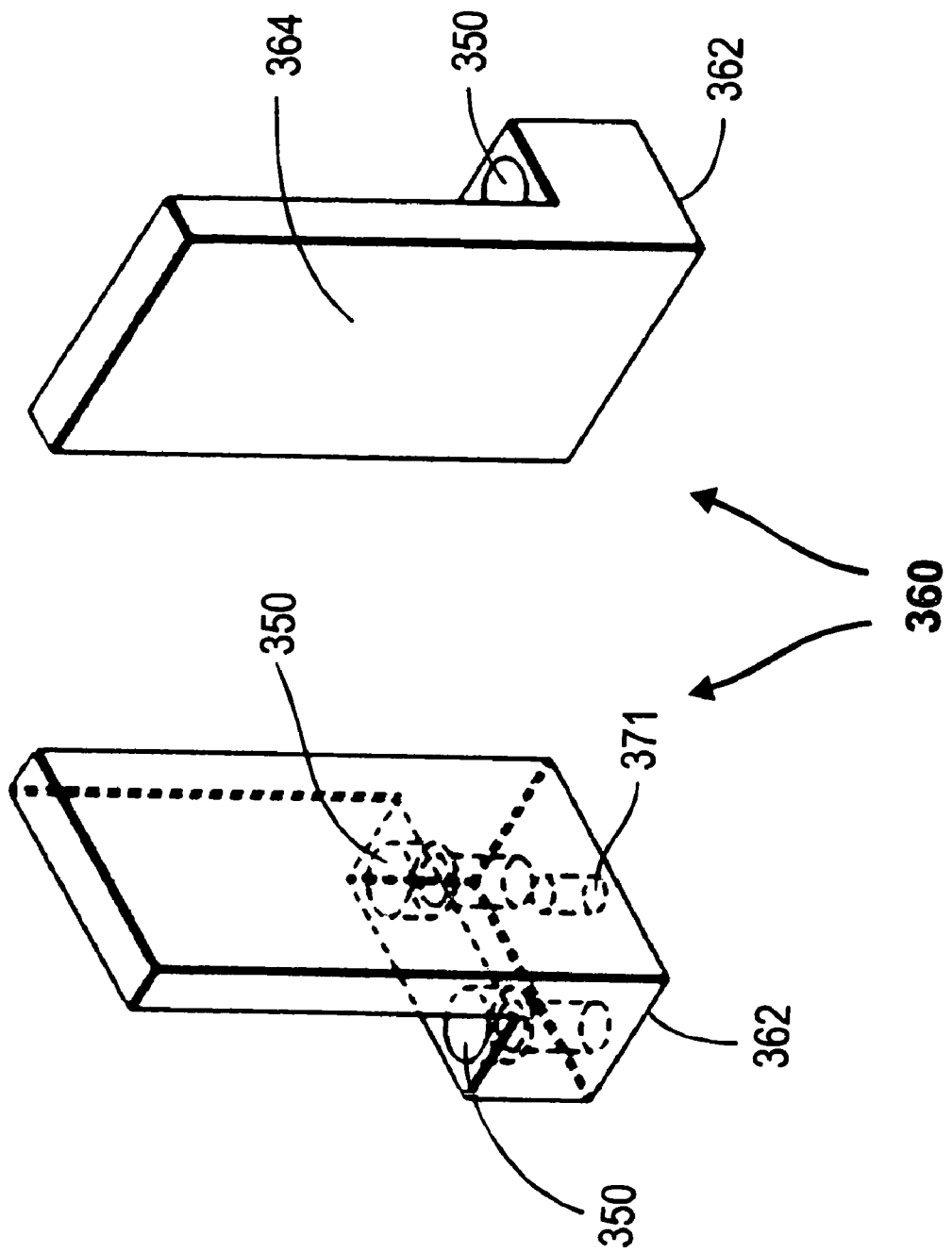
FIG. 12 illustrates a metal grating element with perpendicular faces, that may be mounted to a substrate and used as a component of spectrometer 100.

FIG. 12 illustrates a metal grating element 360 with perpendicular faces 362, 364, that may be mounted to a substrate and used as a component of spectrometer 100. In order to form the grating element 360, a mass of material (e.g., aluminum, aluminum alloys, stainless steel, nickel, copper or beryllium) is first machined to form a face 362 of the grating element, a cylindrical opening 371 that extends from face 362 into the material at an angle perpendicular to face 362, and further cylindrical openings 350 for receiving screws (not shown) that extend from face 362 into the material at an angle perpendicular to face 362. A cylindrical alignment rod (not shown) is inserted into the cylindrical opening 371 such that, after the inserting, the alignment rod extends away from the material at an angle perpendicular to the face 362. A second face 364 of grating element 360 may be fabricated using an epoxy replication process.

Figure 13:
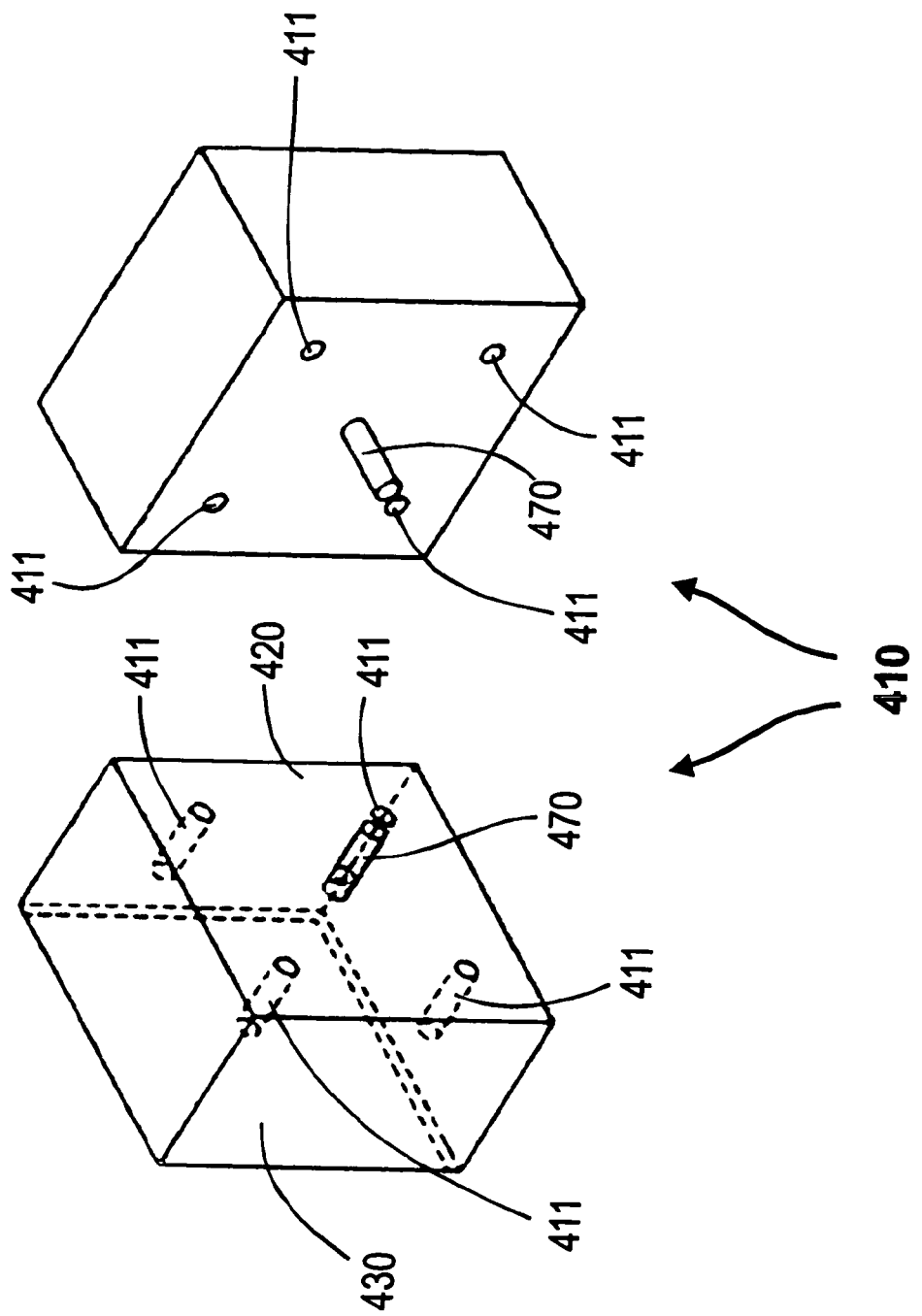
FIG. 13 illustrates an optical grating element having parallel faces, that may be aligned to a mount using the alignment system shown in FIGS. 8-11.

FIG. 13 illustrates a further optical grating element 410 that may be aligned to a mount using the alignment system shown in FIGS. 8-11, and thereafter used as a component of spectrometer 100. In order to form the optical grating element, a mass of material (e.g., aluminum, aluminum alloys, stainless steel, nickel, copper or beryllium) is first machined to form a face 420 of the optical grating element, cylindrical openings 411 (for receiving screws not shown) that extend from face 420 into the material at an angle perpendicular to face 420, and a further cylindrical opening for receiving a cylindrical alignment rod 470 that extends from face 420 into the material at an angle perpendicular to the face 420. Cylindrical alignment rod 470 is inserted into the further cylindrical opening such that, after the inserting, alignment rod 470 extends away from the material at an angle perpendicular to the face 420. A second face 430 of optical grating element 410 is fabricated using an epoxy replication process. Second face 430 may be parallel to the first face 420 as shown in FIG. 13. In further embodiments of the optical grating elements shown in FIGS. 12-13, the second face may be positioned at any angle between parallel and perpendicular with respect to the first face.

Finally, it will be appreciated by those skilled in the art that changes could be made to the embodiments described above without departing from the broad inventive concept thereof. It is understood, therefore, that this invention is not limited to the particular embodiments disclosed, but is intended to cover modifications within the spirit and scope of the present invention as defined in the appended claims.

What is claimed is:

1. A method for aligning and coupling an optical component to a substrate with a precision of at least 12.5 microns in position and 0.075 degrees in angular orientation, comprising:

(a) machining an optical component from a material selected from the group consisting of at least one of aluminum, aluminum alloys, stainless steel, nickel, copper and beryllium;

(b) affixing the optical component to a mount having a flat bottom surface that defines a first plane, wherein a cylindrical rod extends away from the flat bottom surface of the mount at an angle perpendicular to the first plane, and wherein at least first and second screws are disposed in first and second cylindrical openings that extend through the bottom surface of the mount, the first and second cylindrical openings in the mount being aligned perpendicular to the first plane and having an inner diameter that matches an outer diameter of the first and second screws;

(c) providing a substrate having a flat upper surface that defines a second plane, wherein a first cylindrical opening extends from the upper surface of the substrate into the substrate at an angle perpendicular to the second plane, and wherein at least second and third threaded openings extend from the upper surface of the substrate into the substrate at an angle perpendicular to the second plane;

(d) positioning the mount with respect to the substrate by simultaneously aligning the metal rod with the first opening in the substrate, the first opening in the mount with the second threaded opening in the substrate, and the second opening in the mount with the third threaded opening in the substrate;

(e) while the mount and the substrate are aligned, inserting the cylindrical rod into the first cylindrical opening in the substrate until the bottom surface of the mount contacts the upper surface of the substrate, wherein, following said inserting, friction between the cylindrical rod and the first opening in the substrate inhibits rotation of the mount about an axis perpendicular to the first and second planes and tightness between the first opening in the substrate and the cylindrical rod restricts lateral movement of the mount with respect to the substrate; and (f) after step (e), rotating the first and second screws into the second and third threaded openings respectively in the substrate, whereby the mount is coupled to the substrate with said precision.

2. The method of claim 1, wherein the first and second cylindrical openings in the mount include ends having a first tapered shape, and the first and second screws have heads with a second tapered shape that mates with the first tapered shape, whereby the first and second screws are aligned with the first and second cylindrical openings in the mount.

3. The method of claim 1, wherein step (b) further comprises pressing the cylindrical rod into a further cylindrical opening in the mount.

4. The method of claim 3 wherein prior to the pressing step, an outer diameter of the cylindrical rod is greater than an inner diameter of the further cylindrical opening in the mount.

5. The method of claim 3 wherein the inserting in step (e) comprises pressing the cylindrical rod into the first cylindrical opening in the substrate, and, prior to the pressing in step (e), an outer diameter of the first cylindrical rod is greater than an inner diameter of the first cylindrical opening in the substrate.

6. A method for aligning and coupling an optical component to a mount with a precision of at least 12.5 microns in position and 0.075 degrees in angular orientation, comprising:

(a) machining an optical component from a material selected from the group consisting of at least one of aluminum, aluminum alloys, stainless steel, nickel, copper and beryllium, wherein said machining includes forming at least first, second and third cylindrical openings in the material, and said second and third cylindrical openings in the material are threaded;

(b) providing a cylindrical rod positioned in the first cylindrical opening in the machined optical component, wherein the cylindrical rod extends away from a flat back surface of the optical component at an angle perpendicular to the flat back surface;

(c) providing a mount having a flat front surface and at least first, second and third cylindrical openings that extend from the flat front surface into the mount at an angle perpendicular to the flat front surface, wherein at least first and second of the plurality of cylindrical openings in the mount pass completely through a thickness of the mount, wherein first and second screws are respectively disposed in the first and second cylindrical openings in the mount, the first and second screws having an outer diameter that matches an inner diameter of the first and second cylindrical openings in the mount;

(d) after step (b), positioning the mount with respect to the optical component by simultaneously aligning the metal rod extending from the optical component with the third opening in the mount, the second threaded opening in the optical component with the first opening in the mount, and third threaded opening in the optical component with the second opening in the mount;

(e) while the mount and the optical component are aligned, pressing the cylindrical rod into the third cylindrical opening in the mount until the back surface of the optical component contacts the front surface of the mount, wherein, following said inserting, friction between the cylindrical rod and the third opening in the mount inhibits rotation of the mount about an axis perpendicular to the front and back surfaces and tightness between the third cylindrical opening in the mount and the cylindrical rod restricts lateral movement of the mount with respect to the optical component; and (f) after step (e), rotating the first and second screws into the second and third threaded openings respectively in the optical component, whereby the mount is coupled to the optical component with said precision.

7. The method of claim 6, wherein step (a) comprises machining a fourth threaded cylindrical opening in the material, the mount includes a fourth cylindrical opening that extends from the flat front surface into the mount at an angle perpendicular to the flat front surface, wherein the fourth cylindrical opening in the mount passes completely through a thickness of the mount, wherein a third screw is disposed in the fourth cylindrical opening in the mount, the third screw having an outer diameter that matches an inner diameter of the fourth cylindrical opening in the mount, step (f) further comprising rotating the fourth screw into the fourth threaded opening in the optical component.

8. The method of claim 6, wherein prior to the pressing in step (e), an outer diameter of the cylindrical rod is greater than an inner diameter of the third cylindrical opening in the mount.

9. The method of claim 6 wherein step (b) further comprises pressing the cylindrical rod into the first cylindrical opening in the machined optical component.

10. The method of claim 6, wherein prior to the pressing in step (b), an outer diameter of the cylindrical rod is greater than an inner diameter of the first cylindrical opening in the machined optical component.

* * * * *